(12) United States Patent
Ling et al.

(10) Patent No.: US 8,778,932 B2
(45) Date of Patent: Jul. 15, 2014

(54) DIHYDRO-OXAZOLOBENZODIAZEPINONE COMPOUNDS, A PROCESS FOR THERE PREPARATION AND PHARMACEUTICAL COMPOSITIONS CONTAINING THEM

(75) Inventors: István Ling, Budabest (HU); József Barkóczy, Budapest (HU); Ferenc Antoni, Edinburgh (GB); István Gascályi, Budapest (HU); György Lévay, Budakeszi (HU); Michael Spedding, Le Vesinet (FR); László Hársing, Budapest (HU)

(73) Assignees: Les Laboratoires Servier, Suresnes Cedex (FR); Egis Gyogyszergyar Nyrt, Budapest (HU)

( * ) Notice: Subject to any disclaimer, the term of this patent is extended or adjusted under 35 U.S.C. 154(b) by 220 days.

(21) Appl. No.: 13/413,977

(22) Filed: Mar. 7, 2012

(65) Prior Publication Data

US 2012/0232065 A1  Sep. 13, 2012

(30) Foreign Application Priority Data

Mar. 8, 2011 (FR) ..................... 11 00682

(51) Int. Cl.
*A61K 31/551* (2006.01)
*C07D 498/04* (2006.01)
*C07D 519/00* (2006.01)

(52) U.S. Cl.
CPC ............ *C07D 498/04* (2013.01); *C07D 519/00* (2013.01); *A61K 31/551* (2013.01)
USPC .......................................... 514/220; 540/557

(58) Field of Classification Search
CPC ... A61K 31/551; C07D 498/04; C07D 519/00
USPC .......................................... 514/220; 540/557
See application file for complete search history.

(56) References Cited

FOREIGN PATENT DOCUMENTS

WO  WO99/07708  2/1999
WO  WO01/04122  1/2001

OTHER PUBLICATIONS

French Preliminary Search Report for FR1100682 of Sep. 1, 2011.
Ade, et al., J. Neurosci., 2008, 28, 1185-1197.
Akbarian, et al., Cereb. Cortex, 1995, 5, 550-560.
Akbarian, et al., Arch. Gen. Psychiatry, 1995, 52, 258-266.
Atack, et al., Neuropharmacology, 2005, 49, 220-229.
Atack, et al., Neuropharmacology, 2006, 51, 1023-1029.
Badner, et al., Mol. Psychiatry, 2002, 7, 405-411.
Ballard, et al., Psychopharmacology, 2009, 202, 207-223.
Benes, et al., Neuropsychopharmacology, 2001, 25, 1-27.
Bonin, et al., J. Neurophysiol., 2007, 98, 2244-2254.
Chao, et al., Nature, 2010, 468, 263-269.
Cheng, et al., J. Neurosci., 2006, 26, 3713-3720.
Clarkson, et al., Nature, 2010, 468, 305-309.
D'Hulst, et al., Trends Neurosci., 2007, 30, 425-431.
Everaert, et al., Clin. Psychol, Rev., 2012, 32, 413-424,.
Fernandez, et al., Nat. Neurosci., 2007, 10, 411-413.
Foa, Dialogues Clin. Neurosci., 2010, 12, 199-207.
Gueze, et al., Mol. Psychiatry, 2008, 13, 74-83, 73.
Goddard, et al., Arch. Gen. Psychiatry, 2001, 58, 556-561.
Hahn-Barma, et al., J. Neurol. Neurosurg. Psychiatry, 1998, 64, 172-177.
Hasler, et al., Arch. Gen. Psychiatry, 2007, 64, 193-200.
Klausberger, et al., Science, 2008, 321, 53-57.
Kleppner, et al., Expert Opin. Ther. Targets, 2001, 5, 219-239.
Klumpers, et al., Eur. J. Nucl. Med. Mol. Imaging, 2010, 27, 565-574.
Krystal, et al., Mol. Psychiatry, 2002, 7, S71-S80.
Lawrence, et al., Brain, 1998, 121 (Pt. 7), 1329-1341.
Maciag, et al., Biol. Psychiatry, 2010, 67, 465-470.
Martin, et al., J. Neurosci., 2010, 30, 5269-5282.
Möhler, et al., Neuropharmacology, 2012, 62, 42-53.
Nikolaus, et al.., Rev. Neurosci., 2010, 21, 119-139.
Spargo, et al., J. Neurol. Neurosurg, Psychiatry, 1993, 56, 487-491.
Vaiva, et al., Biol. Psychiatry, 2004, 55, 250-254.
Vaiva, et al., Am. J. Psychiatry, 2006, 163, 1446-1448.
Vinkers, et al., Expert Opinion on Investigational Drugs, 2010, 19, 1217-1233.
Volk, et al., Arch. Gen. Psychiatry, 2000, 57, 237-245.
Wisden, et al., J. Neurosci., 1992, 12, 1040-1062.

*Primary Examiner* — Brenda Coleman
(74) *Attorney, Agent, or Firm* — Hueschen and Sage

(57) ABSTRACT

Compounds of formula (I):

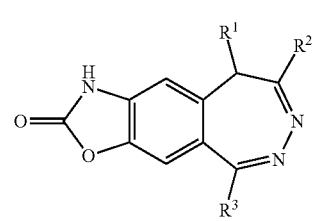

(I)

wherein:
 $R^1$ represents a hydrogen atom or an alkyl group;
 $R^2$ represents an alkyl group;
 $R^3$ represents an aryl or heteroaryl group.
Medicinal products containing the same which are useful in the treatment or prevention of psychiatric and neurological disorders characterized by cognitive deficits.

12 Claims, 3 Drawing Sheets

Figure 1:

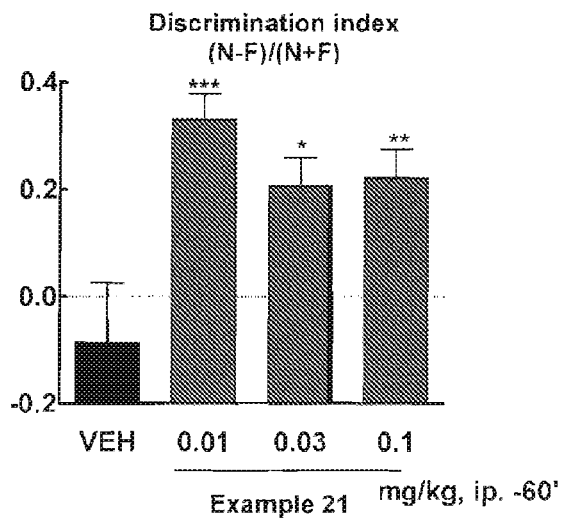

Procognitive effect of the compound of Example 21 in the object recognition model in the mouse after i.p. administration (approx. at the concentration peak).

Mean values ± S.E.M. (n = 20-22/group); Dunnett test following ANOVA (*: $p < 0.05$, : $p < 0.01$, *: $p < 0.001$). Discrimination index:

$$ID = \frac{\text{Duration of new object exploration (s)} - \text{Duration of familiar object exploration (s)}}{\text{Duration of new object exploration (s)} + \text{Duration of familiar object exploration (s)}}$$

Figure 2:

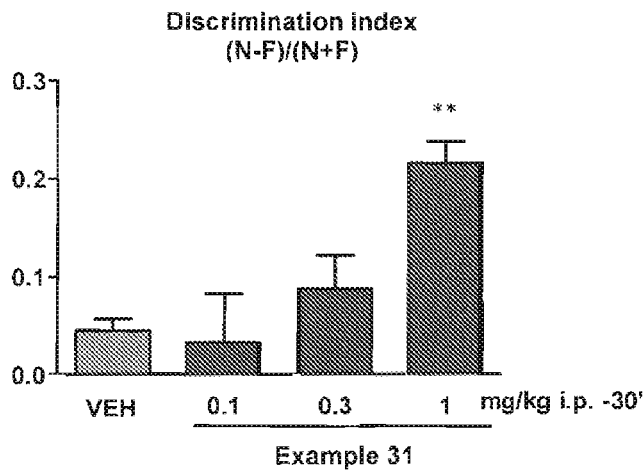

Procognitive effect of the compound of Example 31 in the object recognition model in the mouse after i.p. administration (approx. at the concentration peak).

Mean values ± S.E.M. (n = 12/group); Dunnett test following ANOVA (**: $p < 0.01$).

Figure 3:

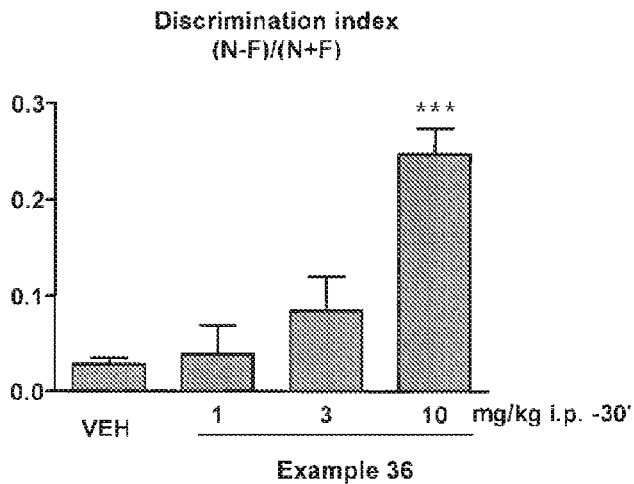

Procognitive effect of the compound of Example 36 in the object recognition model in the mouse after i.p. administration (approx. at the concentration peak).

Mean values ± S.E.M. (n = 12/group); Dunnett test following ANOVA (***: $p < 0.001$).

Figure 4:

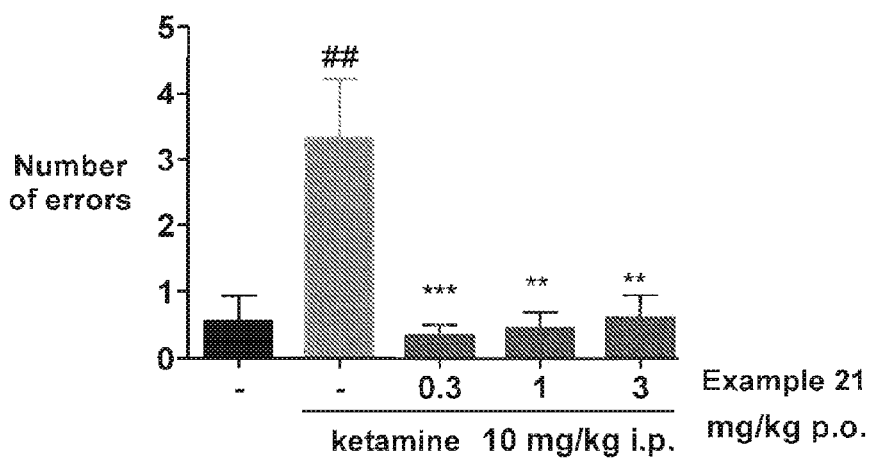

Reduction in the ketamine-induced working memory deficit due to the compound of Example 21, in the rat after p.o. administration Mean values ± S.E.M. (n = 9-10); Mann-Whitney U test (## $p < 0.01$, control vs. control treated with carrier); Dunn test after Kruskal-Wallis ANOVA ( $p < 0.01$, * $p < 0.001$ vs. control treated with ketamine).

Neuroprotective effects of the compound of Example 21 in the permanent MCA occlusion model, in the mouse after i.p. administration Mean values ± S.E.M. (n = 6-8/group); Dunn test following ANOVA ( $p < 0.01$, * $p < 0.001$ vs. control); MC: 0.4 % methylcellulose.

DIHYDRO-OXAZOLOBENZODIAZEPINONE COMPOUNDS, A PROCESS FOR THERE PREPARATION AND PHARMACEUTICAL COMPOSITIONS CONTAINING THEM

The present invention relates to new 1,9-dihydro-2H-[1,3] oxazolo[4,5-h][2,3]benzodiazepin-2-one compounds, to a process for their preparation and to pharmaceutical compositions containing them.

γ-Amino-butyric acid (or GABA) is the predominant inhibitory neurotransmitter in the mammalian central nervous system. In the prosencephalon, GABA is mainly synthesised by interneurons which co-ordinate complex neuronal circuits via $GABA_A$ and $GABA_B$ receptors. The $GABA_A$ receptors are ionotropic heteropentameric chloride channels, comprising protein subunits α (6 genes), β (3 genes) and γ (3 genes) in a ratio of 2:2:1.

Benzodiazepines enhance the action of GABA on $GABA_A$ receptors by interacting on the modulator binding sites. Non-selective benzodiazepine agonists bring about sedative, hypnotic, anxiolytic, anti-convulsant, amnesic, anti-nociceptive and myorelaxant effects.

Knock-in genetic experiments have shown that the $α_3$ subunit is responsible for the sedative effects whilst the $α_2$ and possibly $α_3$ subunits are responsible for the anxiolytic effects of benzodiazepine agonists. Ligands of the benzodiazepine binding sites which produce contrary effects by means of reduction of the activation of the $GABA_A$ receptor brought about by GABA are called "inverse agonists". Such compounds exhibit beneficial activity against cognitive disorders; however, undesirable proconvulsant and anxiogenic effects have prevented further more detailed clinical studies from being carried out on these compounds.

The functions of the $GABA_A$ receptor containing the $α_5$ subunit are less well defined. In the mouse, deletion or reducing the number of $GABA_A$ receptors containing the $α_5$ subunit is associated with an improvement in cognitive functions. Moreover, treatment with a selective $α_5$ inverse agonist produces an improved precognitive effect in several rodent models, whilst in humans a procognitive effect on the memory deficit caused by alcohol has been observed.

There exists a large, unsatisfied need in the treatment of cognitive deficits associated with various age-related disorders, neurodegenerative or vascular disorders and also schizophrenia. Current treatments for Alzheimer's disease, the pathology with the greatest prevalence, are based either on inhibition of cholinesterase (e.g. donepezil) or on NMDA antagonism (memantine). However, cholinesterase inhibitors have a large number of undesirable effects relating to their mechanism of action, whilst the true efficacy of memantine is limited. Consequently, having new therapies of greater efficacy and better tolerability would be especially valuable.

Besides the fact that they are new, the compounds of this invention have especially valuable properties as a result of selectively binding to a $GABA_A$ receptor sub-type and reducing the effects of GABA.

More specifically, the present invention relates to compounds of formula (I):

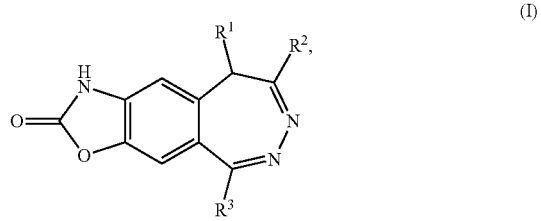

(I)

wherein:
$R^1$ represents a hydrogen atom or a linear or branched $(C_1-C_4)$alkyl group;
$R^2$ represents a linear or branched $(C_1-C_4)$alkyl group;
$R^3$ represents an aryl or heteroaryl group;
their positional isomers, their enantiomers, their diastereoisomers, and also their addition salts with a pharmaceutically acceptable acid, their solvates, their complexes and their adducts.

Among the pharmaceutically acceptable acids there may be mentioned, without implying any limitation, hydrochloric acid, hydrobromic acid, sulphuric acid, acetic acid, trifluoroacetic acid, lactic acid, malonic acid, succinic acid, glutamic acid, fumaric acid, maleic acid, phosphoric acid, citric acid, oxalic acid, methanesulphonic acid, benzenesulphonic acid, para-toluenesulphonic add, camphoric acid, etc.

An aryl group is understood to mean a naphthyl group, optionally substituted by one or more identical or different groups selected from a halogen atom; a linear or branched $(C_1-C_6)$alkyl group which is unsubstituted or substituted by one or more halogen atoms; a linear or branched $(C_1-C_6)$alkoxy group; a linear or branched $(C_1-C_6)$alkylcarbonyl group; a carboxy group; a linear or branched $(C_1-C_6)$alkoxycarbonyl group; a hydroxy group; a cyano group; a nitro group; an aminocarbonyl group which is unsubstituted or substituted by one or more linear or branched $(C_1-C_6)$alkyl groups; or an amino group which is unsubstituted or substituted by one or two linear or branched $(C_1-C_6)$alkyl groups.

A heteroaryl group is understood to mean a bicyclic or tricyclic group in which at least one of the rings is aromatic, containing from 1 to 3, identical or different, hetero atoms selected from nitrogen, oxygen and sulphur, optionally substituted by one or more identical or different groups selected from a halogen atom; a linear or branched $(C_1-C_6)$alkyl group which is unsubstituted or substituted by one or more halogen atoms; a linear or branched $(C_1-C_6)$alkoxy group; a linear or branched $(C_1-C_6)$alkylcarbonyl group; a carboxy group; a linear or branched $(C_1-C_6)$alkoxycarbonyl group; a hydroxy group; a cyano group; a nitro group; an aminocarbonyl group which is unsubstituted or substituted by one or more linear or branched $(C_1-C_6)$alkyl groups; or an amino group which is unsubstituted or substituted by one or two linear or branched $(C_1-C_6)$alkyl groups.

In the compounds of formula (I), $R^1$ preferably represents a hydrogen atom.

Advantageously, the compounds of formula (I) are compounds wherein $R^2$ represents a methyl group.

The $R^3$ group preferably represents a heteroaryl group.

More especially, compounds of formula (I) to which preference is given are compounds wherein $R^3$ represents a bicyclic aromatic group containing from 1 to 3 identical or different hetero atoms selected from nitrogen, oxygen and sulphur, optionally substituted by one or more identical or different groups selected from a halogen atom; a linear or branched $(C_1-C_6)$alkyl group which is unsubstituted or substituted by one or more halogen atoms; a linear or branched $(C_1-C_6)$ alkoxy group; a linear or branched $(C_1-C_6)$alkylcarbonyl group; a carboxy group; a linear or branched $(C_1-C_6)$alkoxycarbonyl group; a hydroxy group; a cyano group; a nitro group; an aminocarbonyl group which is unsubstituted or substituted by one or more linear or branched $(C_1-C_6)$alkyl groups; an amino group which is unsubstituted or substituted by one or two linear or branched $(C_1-C_6)$alkyl groups.

Compounds of formula (I) to which preference is given are compounds wherein $R^3$ represents a benzothienyl, benzofuryl or quinolyl group, optionally substituted by one or more identical or different groups selected from a halogen atom and a linear or branched $(C_1-C_4)$alkyl group which is unsubstituted or substituted by one or more halogen atoms.

Other compounds of the invention to which preference is given are those wherein $R^3$ represents a 1-benzothienyl or 6-quinolyl group, optionally substituted by one or more identical or different groups selected from a halogen atom and a linear or branched $(C_1-C_4)$alkyl group which is unsubstituted or substituted by one or more halogen atoms.

Another advantageous possibility consists of $R^3$ representing a 1-benzothienyl group, optionally substituted by one or more identical or different groups selected from a halogen atom and a linear or branched $(C_1-C_4)$alkyl group which is unsubstituted or substituted by one or more halogen atoms.

The $R^3$ group represents a 1-benzothien-2-yl group, optionally substituted by one or more identical or different groups selected from a halogen atom and a linear or branched $(C_1-C_4)$alkyl group which is unsubstituted or substituted by one or more halogen atoms.

Substitutions of a heteroaryl group to which preference is given are a halogen atom such as fluorine, chlorine, bromine or iodine, more especially fluorine or chlorine; a trifluoromethyl group; or a methyl group.

Preferred compounds of the invention are:

5-(4-fluoro-1-benzothien-2-yl)-8-methyl-1,9-dihydro-2H-[1,3]oxazolo[4,5-h][2,3]-benzodiazepin-2-one;

8-methyl-5-(6-quinolyl-1,9-dihydro-2H-[1,3]oxazolo[4,5-h][2,3]benzodiazepin-2-one;

5-(1-benzothien-2-yl)-8-methyl-1,9-dihydro-2H-[1,3]oxazolo[4,5-h][2,3]benzodiazepin-2-one;

5-(5-chloro-1-benzothien-2-yl)-8-methyl-1,9-dihydro-2H-[1,3]oxazolo[4,5-h][2,3]-benzodiazepin-2-one;

5-[3-chloro-4-(trifluoromethyl)-1-benzothien-2-yl]-8-methyl-1,9-dihydro-2H-[1,3]oxazolo[4,5-h][2,3]benzodiazepin-2-one;

8-methyl-5-[4-(trifluoromethyl)-1-benzothien-2-yl]-1,9-dihydro-2H-[1,3]oxazolo[4,5-h][2,3]benzodiazepin-2-one;

5-(6-fluoro-1-benzothien-2-yl)-8-methyl-1,9-dihydro-2H-[1,3]oxazolo[4,5-h][2,3]-benzodiazepin-2-one;

5-(7-fluoro-1-benzothien-2-yl)-8-methyl-1,9-dihydro-2H-[1,3]oxazolo[4,5-h][2,3]-benzodiazepin-2-one.

Addition salts with a pharmaceutically acceptable acid and also solvates, complexes and adducts of the preferred compounds of the invention form an integral part of the invention.

The invention relates also to a process for the preparation of compounds of formula (I), which process is characterised in that there is used as starting material a compound of formula (II):

(II)

wherein $R^1$ and $R^2$ are as defined for formula (I),
which compound of formula (II), in free form or salt form, is then subjected to a cyclisation reaction in the presence of 1,1'-carbonyldiimidazole to yield the compound of formula (III):

(III)

wherein $R^1$ and $R^2$ are as defined for formula (I),
which is reacted with a reducing agent to yield the compound of formula (IV):

(IV)

wherein $R^1$ and $R^2$ are as defined for formula (I),
which is then subjected to the action of the compound of formula (V):

$$R^3\text{—CHO} \quad (V),$$

wherein $R^3$ is as defined for formula (I),
to yield the compound of formula (VI):

(VI)

wherein $R^1$, $R^2$ and $R^3$ are as defined for formula (I),
which is then subjected to the action of an oxidising agent, followed by formation of a salt, to yield the compound of formula (VII):

(VII)

wherein $R^1$, $R^2$ and $R^3$ are as defined for formula (I) and X represents a counter-ion such as $ClO_4^-$, $Cl^-$, $Br^-$, $HsO_4^-$,
which is then subjected to the action of hydrazine to yield the compound of formula (I),
which compound of formula (I) may then be purified according to a conventional separation technique, is converted, if desired, into its addition salts with a pharmaceutically acceptable acid and is separated, where appropriate, into its isomers, if they exist, according to a conventional separation technique.

An advantageous variant relates to a process for the preparation of compounds of formula (I), which process is characterised in that there is used as starting material the compound of formula (III):

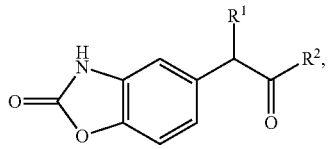

wherein R¹ and R² are as defined for formula (I),
which is subjected to a bromination reaction to yield the compound of formula (VIII):

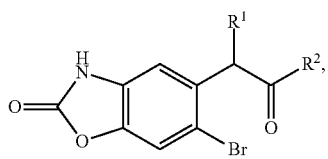

wherein R¹ and R² are as defined for formula (I),
which is subjected to a step of protection of the carbonyl group to yield the compound of formula (IX):

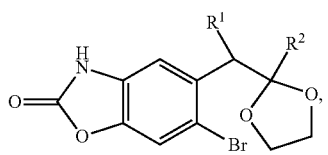

wherein R¹ and R² are as defined for formula (I),
which is then subjected to the action of the compound of formula (X):

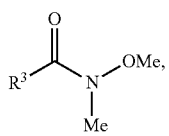

wherein R³ is as defined for formula (I),
to yield the compound of formula (XI):

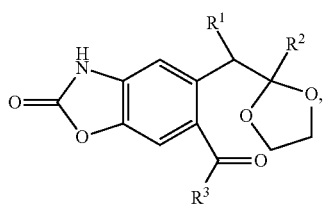

wherein R¹, R² and R³ are as defined for formula (I), which is then subjected to a cyclisation reaction to yield the compound of formula (VII):

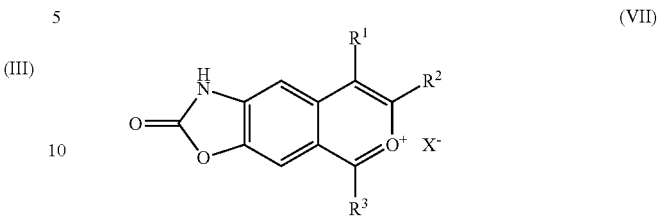

wherein $R^1$, $R^2$ and $R^3$ are as defined for formula (I) and X represents a counter-ion such as $ClO_4^-$, $Cl^-$, $HSO_4^-$,
which is then subjected to the action of hydrazine to yield the compound of formula (I),
which compound of formula (I) may then be purified according to a conventional separation technique, is converted, if desired, into its addition salts with a pharmaceutically acceptable acid and is separated, where appropriate, into its isomers, if they exist, according to a conventional separation technique.

BRIEF DESCRIPTION OF THE DRAWINGS

FIG. 1: Procognitive effect of the compound of Example 21 in the object recognition model in the mouse after i.p. administration (approx. at the concentration peak).

FIG. 2: Procognitive effect of the compound of Example 31 in the object recognition model in the mouse after i.p. administration (approx, at the concentration peak).

FIG. 3: Procognitive effect of the compound of Example 36 in the object recognition model in the mouse after i.p. administration (approx. at the concentration peak).

FIG. 4: Reduction in the ketamine-induced working memory deficit due to the compound of Example 21, in the rat after p.o. administration.

DETAILED DESCRIPTION OF THE INVENTION

Figure 5:
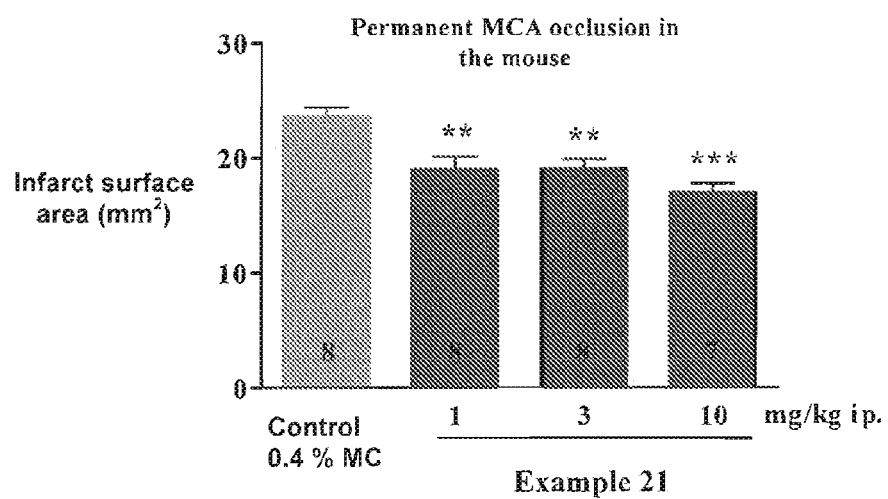
FIG. 5: Neuroprotective effects of the compound of Example 21 in the permanent MCA occlusion model, in the mouse after i.p, administration.

The compounds of formulae (II), (V) and (X) are commercially available or readily accessible to the person skilled in the art using conventional chemical reactions or chemical reactions described in the literature.

The compounds of the present invention are selective for the subunit of the $GABA_A$ receptor and reduce the effects of the neurotransmitter GABA, making them useful in the treatment or prevention of psychiatric and neurological disorders characterised by cognitive deficits, such as schizophrenia, unipolar depression, Alzheimer's disease, vascular dementia, autism spectrum disorders, Down's syndrome, fragile X syndrome, Parkinson's disease, Huntington's disease. Other possible therapeutic indications are related to various anxiety states such as generalised anxiety, panic disorder with or without agoraphobia, obsessive-compulsive disorders, post-traumatic stress disorders and bipolar disorders. The compounds of the invention may be used in the treatment of sequelae of a cerebral vascular accident and sequelae of brain, spine or medullary trauma.

The compounds will preferably be used in the treatment or prevention of Alzheimer's disease, vascular dementia such as dementia due to the consequences of a cerebral vascular accident, Huntington's disease and Down's syndrome.

The invention relates also to pharmaceutical compositions comprising, as active ingredient, at least one compound of formula (I) on its own or in combination with one or more inert, non-toxic excipients or carriers. Among the pharmaceutical compositions according to the invention there may be mentioned more especially those that are suitable for oral, parenteral (intravenous or subcutaneous) or nasal administration, tablets or dragées, sublingual tablets, capsules, lozenges, suppositories, creams, ointments, dermal gels, injectable preparations and drinkable suspensions.

The useful dosage varies according to the age and weight of the patient and the nature and severity of the disorder, and also the administration route, which may be nasal, rectal, parenteral or oral. Generally, the unit dose ranges from 0.1 to 1000 mg per 24 hours for treatment in 1 to 3 administrations.

The Examples that follow illustrate the invention but do not limit it in any way. The structures of the described compounds were confirmed by customary spectroscopic techniques (including proton NMR: is =large singlet; s=singlet; d=doublet; t=triplet; dd=doublet of doublets; m=multiplet).

The Preparations described hereinbelow yield starting compounds that are used in the synthesis of compounds of the invention.

Preparation 1:
5-(2-hydroxypropyl)-1,3-benzoxazol-2(3H)-one

Step A: 5-(2-axopropyl)-1,3-benzoxazol-2(3H)-one

To a solution of (3-amino-4-hydroxyphenyl)acetone hydrochloride (prepared according to EP 101 223; *Chemistry Letters* 1980, 1, 85-88; or *J. Org. Chem.* 1951, 16, 221-224) (250 mmol) in tetrahydrofuran (509 mL) there is added 1,1'-carbonyldiimidazole (48.25 g; 290 mmol) and the mixture is refluxed for 2 hours. After cooling to ambient temperature, the precipitate is filtered off and the filtrate is evaporated in vacuo. The residue is dissolved in ethyl acetate (400 mL), the solution is washed with 5% aqueous HCl solution (2×200 mL) and with brine (2×200 mL), and then the organic phase is concentrated in vacuo to yield the title product in the form of a solid.
Melting point: 115-116° C.

Step 5-(2-hydroxypropyl)-1,3-benzoxazol-2(3H)-one

To a solution of the product of the Step above ON mmol) in ethyl acetate (352 mL) and water (120 mL) there is added, several times, sodium borohydride (2.1 g; 550 mmol) over 20 minutes at 0-10° C. The reaction mixture is stirred at ambient temperature until the reaction is complete. The mixture is then treated with 10% aqueous HCl solution until the pH is 2 and; after separation of the phases, the aqueous phase is extracted with ethyl acetate (3×90 mL). The organic phases are collected, dried over sodium sulphate and concentrated in vacuo. The solid residue is suspended in diisopropyl ether and then filtered off to yield the title product in the form of a solid.
Melting point: 133-134° C.

Preparation 2: 5-(1-ethyl-2-hydroxypropyl)-1,3-benzoxazol-2(3H)-one

The title product is obtained in accordance with the procedure described in Preparation 1, using, as starting reagent, 3-(3-amino-4-hydroxyphenyl)-2-pentanone hydrochloride instead of 1-(3-amino-4-hydroxyphenyl)acetone hydrochloride.
Melting point: 107-109° C.

Preparation 3: 5-[1-(1-hydroxyethyl)butyl]-1,3-benzoxazol-2(3H)-one

The title product is obtained in the form of an oil in accordance with the procedure described in Preparation 1, using, as starting reagent, 2-amino-4-[1-(1-hydroxyethyl)butyl]phenol hydrochloride instead of 1-(3-amino-4-hydroxyphenyl)acetone hydrochloride.

Preparation 4:
5-(2-hydroxybutyl)-1,3-benzoxazol-2(3H)-one

The title product is obtained in accordance with the procedure described in Preparation 1, using, as starting reagent, 1-(3-amino-4-hydroxyphenyl)-2-butanone hydrochloride instead of 1-(3-amino-4-hydroxyphenyl)acetone hydrochloride.
Melting paint: 117-119° C.

Example 1

8-methyl-5-(2-naphthyl)-1,9-dihydro-2H-[1,3]oxazolo[4,5-h][2,3]-benzodiazepin-2-one Step A: 7-methyl-5-(2-naphthyl)-1,5,7,8-tetrahydro-2H-isochromeno[6,7-d]-[1,3]oxazol-2-one To a suspension of the compound of Preparation 1 (97.0 mmol) and 2-naphthaldehyde (94.3 mmol) in ethyl acetate (180 mL) there is added a 15% anhydrous HCl solution in ethyl acetate (90 mL). The reaction mixture is stirred for 20 hours at ambient temperature. Precipitation is observed and the expected product in the form of a powder is collected by filtration.
Melting point: 220-222° C.

Step B: 7-methyl-5-(2-naphthyl)-2-oxo-1H,2H-isochromeno[6,7-d][1,3]oxazol-6-ium perchlorate To a solution of the product of the Step above (67.5 mmol) in acetone (490 mL) there is added, dropwise, Jones reagent (88.63 mL; 236 mmol) at 0-10° C. over 40 minutes. The mixture is stirred at ambient temperature until the reaction ceases and is then poured into ice-cold water (2200 mL). The precipitate is filtered off, washed with water (5×50 mL), dried and then directly reacted in the next step.

To a suspension of dry product in ethyl acetate (460 mL), under reflux, there is added perchloric acid 70% (5.87 mL; 67.5 mmol). Reflux is maintained for a further 60 minutes, with vigorous stirring. After cooling to ambient temperature, the crystals obtained are filtered off and dried to yield the expected product.
Melting point: 304-307° C.

8-methyl-5-(2-naphthyl)-1,9-dihydro-2H-[1,3]oxazolo[4,5-h][2,3]benzodiazepin-2-one To a solution of the product of the Step above (51 mmol) in 2-propanol (468 mL) there is added hydrazine hydrate (6.68 mL; 133 mmol) with vigorous stirring at ambient temperature. The reaction mixture is stirred for 20 hours at ambient temperature. The crystals obtained are then filtered off and stirred in warm water (1900 mL) for 30 minutes. After filtration and drying, the solid is purified in acetonitrile at reflux.
Melting point: 304-306° C.

Example 2

5-(1-benzofuran-2-yl)-8-methyl-1,9-dihydro-2H-[1,3]oxazolo[4,5-h][2,3]benzodiazepin-2-one Step A: 6-bromo-5-(2-oxopropyl)-1,3-benzoxazol-2(3H)-one To a solution of the compound of Preparation 1 (52 mmol) in methanol (150 mL) there is added N-bromosuccinimide (9.8 g; 55 mmol) in small portions at 0-10° C. The mixture is stirred for one hour more and is then evaporated in vamp. The residue obtained is dissolved in ethyl acetate (250 mL), and the organic phase is washed with 5% aqueous sodium hydrogen carbonate solution (4×50 mL), dried over $MgSO_4$ and evaporated in vacuo to yield the expected product in the form of a solid.
Melting point: 160-162° C.

Step B: 6-bromo-5-[(2-methyl-1,3-dioxolan-2-yl)methyl]-1,3-benzoxazol-2(3H)-one

A mixture of the product of the Step above (14.7 g; 54 mmol), ethylene glycol (13.6 mL; 243 mmol), para-toluenesulphonic acid (1 g; 5 mmol) and toluene (300 mL) is refluxed, using a Dean-Stark apparatus, for 6 hours. The solution is cooled to ambient temperature and then poured into ethyl acetate (300 mL). The organic phase is washed with 5% aqueous sodium hydrogen carbonate solution (100 mL), brine (100 mL) and then dried over $MgSO_4$ and evaporated in vacuo. The residue is purified by chromatography over a silica gel column (eluant: dichloromethane/ethyl acetate) to yield the title product in solid form.
Melting point: 117-119° C.

Step C: 6-(1-benzofuran-2-ylcarbonyl)-5-[(2-methyl-1,3-dioxolan-2-yl)methyl]-1,3-benzoxazol-2(3H)-one A 2.5M solution of n-butyllithium in hexane (10.5 mL; 2.6 mmol) is added dropwise to a solution of the product of the Step above (3.1 g; 10 mmol) in tetrahydrofuran (120 mL) at −78° C. The reaction mixture is then warmed to −35° C., stirred for 30 minutes, and then N-methoxy-N-methyl-1-benzofuran-2-carboxamide (16.5 mmol) is added. The reaction mixture is then stirred at −35° C. for 1.5 hours more, and is then poured into saturated ammonium chloride solution (150 mL). After adding ethyl acetate (150 mL), the organic phase is washed with brine (100 mL), dried over $MgSO_4$ and evaporated in vacuo. The residue is purified by chromatography over a silica gel column (eluant: hexane/ethyl acetate) to yield the title product.
Melting point: 213-215° C.

Step D: 5-(1-benzofuran-2-yl)-7-methyl-2-oxo-1H,2H-isochromeno[6,7-d][1,3]-oxazol-6-ium perchlorate To a suspension of the product of the Step above in ethyl acetate (460 mL), under reflux, there is added perchloric acid 70% (5.87 mL; 67.5 mmol). Reflux is maintained for 60 minutes more, with vigorous stirring. After cooling to ambient temperature, the crystals obtained are filtered off and dried to yield the expected product.
Melting point: 318-320° C.

Step E: 5-(1-benzofuran-2-yl)-8-methyl-1,9-dihydro-2H-[1,3]oxazolo[4,5-h][2,3]benzodiazepin-2-one To a solution of the product of the Step above (51 mmol) in 2-propanol (468 mL) there is added hydrazine hydrate (6.68 mL; 133 mmol), with vigorous stirring, at ambient temperature. The reaction mixture is stirred for 20 hours at ambient temperature. The crystals obtained are then filtered off and then stirred in warm water (1900 mL) for 30 minutes. After filtration and drying, the solid is purified in acetonitrile at reflux.
Melting point: 290-292° C.

Example 3

5-(5-chloro-3-methyl-1-benzofuran-2-yl)-8-methyl-1,9-dihydro-2H-[1,3]oxazolo[4,5-h][2,3]benzodiazepin-2-one The title product is obtained according to the procedure described in Example 2 using 5-chloro-N-methoxy-N,3-dimethyl-1-benzofuran-2-carboxamide instead of N-methoxy-N-methyl-1-benzofuran-2-carboxamide.
Melting point: 297-298° C.

Example 4

8-methyl-5-(2-quinolyl)-1,9-dihydro-2H-[1,3]oxazolo[4,5-h][2,3]-benzodiazepin-2-one To a solution of 7-methyl-2-oxo-5-(2-quinolyl)-1H,2H-isochromeno[6,7-d][1,3]oxazol-6-ium perchlorate (51 mmol) (obtained in Steps A to D described in Example 2 using N-methoxy-N-methyl-2-quinolinecarboxamide instead of N-methoxy-N-methyl-1-benzofuran-2-carboxamide) in 2-propanol (468 mL) there is added hydrazine hydrate (6.68 mL; 133 mmol), with vigorous stirring, at ambient temperature. The reaction mixture is stirred for 20 hours at ambient temperature. The crystals obtained are then filtered off and then stirred in warm water (1900 mL) for 30 minutes. After filtration and drying, the solid is purified by chromatography over a silica gel column (eluant: dichloromethane/methanol) to yield the title product.
Melting point: 304-306° C.

Example 5

8-methyl-5-(6-quinolyl)-1,9-dihydro-2H-[1,3]oxazolo[4,5-h][2,3]-benzodiazepin-2-one To a suspension of 7-methyl-2-oxo-5-(6-quinolyl)-1H,2H-isochromeno[6,7-d][1,3]oxazol-6-ium perchlorate (51 mmol) (obtained according to Steps A to D described in Example 2 using N-methoxy-N-methyl-6-quinolinecarboxamide instead of N-methoxy-N-methyl-1-benzofuran-2-carboxamide) in 2-propanol (468 mL) there is added hydrazine hydrate (6.68 mL; 133 mmol), with vigorous stirring, at ambient temperature. The reaction mixture is stirred for 20 hours at ambient temperature. The crystals obtained are then filtered off and then stirred in warm water (1900 mL) for 30 minutes. After filtration and drying, the solid is purified by crystallising from a dimethylformamide/methanol mixture.

Melting point: 302-304° C.

$^1$H NMR spectroscopic analysis (500 MHz, DMSO, δ in ppm): 12.05 (ls, 1H); 8.95 (dd, 1H, J=4.2 and 1.7 Hz); 8.44 (dd, 1H, J=8.3 and 1.7 Hz); 8.09 (m, 3H); 7.57 (dd, 1H, J=8.3 and 4.2 Hz); 7.29 (s, 1H); 7.24 (s, 1H); 3.64 (d, 1H, J=12.3 Hz); 2.89 (d, 1H, J=12.2 Hz): 2.10 (s, 3H).

Example 6

5-(1-benzothien-2-yl)-8-methyl-1,9-dihydro-2H-[1,3]oxazolo[4,5-h][2,3]benzodiazepin-2-one To a solution of 5-(1-benzothien-2-yl)-7-methyl-1,5,7,8-tetrahydro-2H-isochromeno[6,7-d]oxazol-2-one (67.5 mmol), obtained according to Step A described in Example 1 using 1-benzothiophene-2-carbaldehyde instead of 2-naphthaldehyde, in acetone (490 mL) there is added, dropwise, Jones reagent (88.63 mL; 236 mmol) at 0-10° C. over 40 minutes. The mixture is stirred at ambient temperature until the reaction ceases and is then poured into ice-cold water (2200 mL). The precipitate is filtered off, washed with water (5×50 mL), dried and then directly reacted in the next step. To a suspension of dry product in ethyl acetate (460 mL), under reflux, there is added perchloric acid 70% (5.87 mL; 67.5 mmol). Reflux is maintained for a further 60 minutes, with vigorous stirring. After cooling to ambient temperature, the crude product is isolated and then suspended in 2-propanol (434 mL), and hydrazine hydrate (6.17 mL; 127 mmol) is then added, with vigorous stirring, at ambient temperature. The reaction mixture is stirred for 20 hours at ambient temperature. The crystals obtained are then filtered off and stirred in warm water (1900 mL) for 30 minutes, After filtration and drying, the solid is refluxed in acetonitrile for 30 minutes. After isolation and drying, the title product is obtained.

Melting point: 338-340° C.

$^1$H NMR spectroscopic analysis (500 MHz, DMSO, δ in ppm): 12.10 (ls, 1H); 7.99 (m, 1H); 7.86 (m, 1H); 7.69 (s, 1H); 7.53 (s, 1H); 7.39 (m, 2H); 7.28 (s, 1H); 3.61 (d, 1H, J=12.3 Hz); 2.86 (d, 1H, J=12.2 Hz); 2.08 (s, 3H).

Example 7

5-(3-chloro-4-fluoro-1-benzothien-2-yl)-8-methyl-1,9-dihydro-2H-[1,3]oxazolo[4,5-h][2,3]benzodiazepin-2-one The title product is obtained according to the procedure described in Example 1 using 3-chloro-4-fluoro-1-benzothiophene-2-carbaldehyde instead of 2-naphthaldehyde.

Melting point: 295-297° C.

Example 8

5-(3-chloro-6-fluoro-1-benzothien-2-yl)-8-methyl-1,9-dihydro-2H-[1,3]oxazolo[4,5-h][2,3]benzediazepin-2-one A suspension of 5-(3-chloro-6-fluoro-1-benzothien-2-yl)-7-methyl-2-oxo-1H,2H-isochromeno[6,7-d][1,3]oxazol-6-ium perchlorate (51 mmol) (obtained according to Steps A and B described in Example 1 using 3-chloro-6-fluoro-1-benzothiophene-2-carbaldehyde instead of 2-naphthaldehyde) in 2-propanol (468 mL) there is added hydrazine hydrate (6.68 mL; 133 mmol), with vigorous stirring, at ambient temperature. The reaction mixture is stirred for 20 hours at ambient temperature. The crystals obtained are then filtered off and then stirred in warm water (1900 mL) for 30 minutes. After filtration and drying, the solid is purified by crystallising from a dimethylformamide/methanol mixture.

Melting point: 276-278° C.

Example 9

5-[3-chloro-4-(trifluoromethyl)-1-benzothien-2-yl]-8-methyl-1,9-dihydro-2H-[1,3]oxazolo[4,5-h][2,3]benzodiazepin-2-one The title product is obtained according to the procedure described in Example 1 using 3-chloro-1-(trifluoromethyl)-1-benzothiophene-2-carbaldehyde instead of 2-naphthaldehyde.

Melting point: 322-323° C.

$^1$H NMR spectroscopic analysis (500 MHz, DMSO δ in ppm): 12.02 (ls, 1H); 8.52 (d, 1H, J=8.1 Hz); 7.99 (d, 1H, J=7.5 Hz); 7.72 (1, 1H, J=7.9 Hz); 7.31 (s, 1H); 7.30 (s, 1H); 3.77 (d, 1H, J=12.5 Hz); 2.85 (d, 1H, J=12.3 Hz); 2.13 (s, 3H).

Example 10

8-methyl-5-(3-methyl-1-benzothien-2-yl)-1,9-dihydro-2H-[1,31]-oxazolo[4,5-h][2,3]benzodiazepin-2-one The title product is obtained according to the procedure described in Example 1 using 3-methyl-1-benzothiophene-2-carbaldehyde instead of 2-naphthaldehyde.

Melting point: 301-303° C.

Example 11

8-methyl-5-[3-methyl-4-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 3-methyl-4-(trifluoromethyl)-1-benzothiophene-2-carbaldehyde instead of 2-naphthaldehyde.

Melting point: 313-315° C.

Example 12

8-methyl-5-[3-methyl-5-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 3-methyl-5-(trifluoromethyl)-1-benzothiophene-2-carbaldehyde instead of 2-naphthaldehyde.

Melting point: 301-303° C.

Example 13

8-methyl-5-[3-methyl-6-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 3-methyl-6-(trifluoromethyl)-1-benzothiophene-2-carbaldehyde instead of 2-naphthaldehyde.

Melting point: 303-305° C.

Example 14

8-methyl-5-[3-methyl-7-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 3-methyl-7-(trifluoromethyl)-1-benzothiophene-2-carbaldehyde instead of 2-naphthaldehyde.
Melting point: 292-294° C.

Example 15

5-(3-ethyl-1-benzothien-2-yl)-8-methyl-1,9-dihydro-2H-[1,3]oxazolo[4,5-h][2,3]benzodiazepin-2-one The title product is obtained according to the procedure described in Example 1 using 3-ethyl-1-benzothiophene-2-carbaldehyde instead of 2-naphthaldehyde.
Melting point: 293-295° C.

Example 16

5-(3-ethyl-4-fluoro-1-benzothien-2-yl)-8-methyl-1,9-dihydro-2H-[1,3]oxazolo[4,5-h][2,3]benzodiazepin-2-one To a suspension of 5-(3-ethyl-4-fluoro-1-benzothien-2-yl)-7-methyl-2-oxo-1H,2H-isochromeno[6,7-d][1,3]oxazol-6-ium perchlorate (51 mmol) (obtained according to Steps A and B described in Example 1 using 3-ethyl-4-fluoro-1-benzothiophene-2-carbaldehyde instead of 2-naphthaldehyde) in 2-propanol (468 mL) there is added hydrazine hydrate (6.68 mL; 133 mmol), with vigorous stirring, at ambient temperature. The reaction mixture is stirred for 20 hours at ambient temperature. The crystals obtained are then filtered off and then stirred in warm water (1900 mL) for 30 minutes. After filtration and drying, the solid is purified by chromatography over a silica gel column (eluant: dichloromethane/acetonitrile) to yield the title product.
Melting point: 297-299° C.

Example 17

5-(3-ethyl-4,7-difluoro-1-benzothien-2-yl)-8-methyl-1,9-dihydro-2H-[1,3]oxazolo[4,5-h][2,3]benzodiazepin-2-one The title product is obtained according to the procedure described in Example 8 using 3-ethyl-4,7-difluoro-1-benzothiophene-2-carbaldehyde instead of 3-chloro-6-fluoro-1-benzothiophene-2-carbaldehyde.
Melting point: 270-272° C.

Example 18

8-methyl-5-(3-propyl-1-benzothien-2-yl)-1,9-dihydro-2H-[1,3]-oxazolo[4,5-h][2,3]benzodiazepin-2-one To a suspension of 5-(3-propyl-1-benzothien-2-yl)-7-methyl-2-oxo-1H,2H-isochromeno[6,7-d][1,3]oxazol-6-ium perchlorate (51 mmol) (obtained according to Steps A and B described in Example 1 using 3-propyl-1-benzothiophene-2-carbaldehyde instead of 2-naphthaldehyde) in 2-propanol (468 mL) there is added hydrazine hydrate (6.68 mL; 133 mmol), with vigorous stirring, at ambient temperature. The reaction mixture is stirred for 20 hours at ambient temperature. The crystals obtained are then filtered off and then stirred in warm water (1900 mL) for 30 minutes. After filtration and drying, the solid is purified by chromatography over a silica gel column (eluant: dichloromethane/ethyl acetate) to yield the title product.
Melting point: 307-308° C.

Example 19

5-(3-butyl-1-benzothien-2-yl)-8-methyl-1,9-dihydro-2H-[1,3]oxazolo[4,5-h][2,3]benzodiazepin-2-one The title product is obtained according to the procedure described in Example 18 using 3-butyl-1-benzothiophene-2-carbaldehyde instead of 3-propyl-1-benzothiophene-2-carbaldehyde.
Melting point: 278-280° C.

Example 20

8-methyl-5-[3-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 3-(trifluoromethyl)-1-benzothiophene-2-carbaldehyde instead of 2-naphthaldehyde.
Melting point: 260-262° C.

Example 21

5-(4-fluoro-1-benzothien-2-yl)-8-methyl-1,9-dihydro-2H-[1,3]oxazolo[4,5-h][2,3]benzodiazepin-2-one Step A: 5-(4-fluoro-1-benzothien-2-yl)-7-methyl-2-oxo-1H,2H-isochromeno[6,7-d][1,3]oxazol-6-ium perchlorate The expected product is obtained according to the procedure described in Steps A and B of Example 1 using 4-fluoro-1-benzothiophene-2-carbaldehyde instead of 2-naphthaldehyde, or according to the procedure described in Steps A to D of Example 2 using 4-fluoro-N-methoxy-N-methyl-1-benzothiophene-2-carboxamide instead of N-methoxy-N-methyl-1-benzofuran-2-carboxamide.
Melting point: 278-280° C.

Step B: 5-(4-fluoro-1-benzothien-2-yl)-8-methyl-1,9-dihydro-2H-[1,3]oxazolo[4,5-h][2,3]benzodiazepin-2-one The expected product is obtained, starting from the compound of the Step above, according to the procedure described in Step C of Example 1.
Melting point: 394-396° C.
$^1$H NMR spectroscopic analysis (500 MHz, DMSO, δ in ppm): 12.06 (ls, 1H); 7.86 (d, 1H, J=8.1 Hz); 7.74 (s, 1H); 7.45 (m, 1H); 7.45 (s, 1H); 7.28 (s, 1H); 7.21 (dd, 1H, J1=8.1 Hz, J2=10.4 Hz); 3.62 (d, 1H, J=12.3 Hz); 2.85 (d, 1H, J=12.2 Hz); 2.08 (s, 3H).

Example 22

5-(4-fluoro-3-methyl-1-benzothien-2-yl)-8-methyl-1,9-dihydro-2H-[1,3]oxazolo[4,5-h][2,3]benzodiazepin-2-one The title product is obtained according to the procedure described in Example 1 using 4-fluoro-3-methyl-1-benzothiophene-2-carbaldehyde instead of 2-naphthaldehyde.
Melting point: 321-323° C.

Example 23

9-ethyl-5-(4-fluoro-1-benzothien-2-yl)-8-methyl-1,9-dihydro-2H-[1,3]oxazolo[4,5-h][2,3]benzodiazepin-2-one The title product is obtained according to the procedure described in Example 1 using 4-fluoro-1-benzothiophene-2-carbaldehyde instead of 2-naphthaldehyde and the compound of Preparation 2 instead of the compound of Preparation 1.
Melting point: 291-292° C.

Example 24

5-(4-fluoro-1-benzothien-2-yl)-8-methyl-9-propyl-1,9-dihydro-2H-[1,3]oxazolo[4,5-h][2,3]benzodiazepin-2-one The title product is obtained according to the procedure described in Steps A and B of Example 1 using 4-fluoro-1-benzothiophene-2-carbaldehyde instead of 2-naphthaldehyde and the compound of Preparation 3 instead of the compound of Preparation 1, followed by the procedure described in Example 18.
Melting point: 299-300° C.

Example 25

5-(4-fluoro-3-methyl-1-benzothien-2-yl)-8-methyl-9-propyl-1,9-dihydro-2H-[1,3]oxazolo[4,5-h][2,3]benzodiazepin-2-one The title product is obtained according to the procedure described in Example 1 using 4-fluoro-3-methyl-1-benzothiophene-2-carbaldehyde instead of 2-naphthaldehyde and the compound of Preparation 3 instead of the compound of Preparation 1.
Melting point: 269-271° C.

Example 26

5-(4-fluoro-7-iodo-1-benzothien-2-yl)-8-methyl-1,9-dihydro-2H-[1,3]oxazolo[4,5-h][2,3]benzodiazepin-2-one The title product is obtained according to the procedure described in Example 1 using 4-fluoro-7-iodo-1-benzothiophene-2-carbaldehyde instead of 2-naphthaldehyde.
Melting point: 324-326° C.

Example 27

5-(4-chloro-1-benzothien-2-yl)-8-methyl-1,9-dihydro-2H-[1,3]-oxazolo[4,5-h][2,3]benzodiazepin-2-one The title product is obtained according to the procedure described in Example 6 using 4-chloro-1-benzothiophene-2-carbaldehyde instead of 1-benzothiophene-2-carbaldehyde.
Melting point: 333-335° C.

Example 28

5-(4-chloro-3-methyl-1-benzothien-2-yl)-8-methyl-1,9-dihydro-2H-[1,3]oxazolo[4,5-h][2,3]benzodiazepin-2-one The title product is obtained according to the procedure described in Example 1 using 4-chloro-3-methyl-1-benzothiophene-2-carbaldehyde instead of 2-naphthaldehyde.
Melting point: 305-307° C.

Example 29

5-(4-bromo-1-benzothien-2-yl)-8-methyl-1,9-dihydro-2H-[1,3]-oxazolo[4,5-h][2,3]benzodiazepin-2-one The title product is obtained according to the procedure described in Example 1 using 4-bromo-1-benzothiophene-2-carbaldehyde instead of 2-naphthaldehyde.
Melting point: 336-333° C.

Example 30

5-(4-iodo-1-benzothien-2-yl)-8-methyl-1,9-dihydro-2H-[1,3]oxazolo[4,5-h][2,3]benzodiazepin-2-one The title product is obtained according to the procedure described in Example 1 using 4-iodo-1-benzothiophene-2-carbaldehyde instead of 2-naphthaldehyde.
Melting point: 326-328° C.

Example 31

8-methyl-5-[4-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 4-(trifluoromethyl)-1-benzothiophene-2-carbaldehyde instead of 2-naphthaldehyde.
Melting point: 343-345° C.
$^1$H NMR spectroscopic analysis (500 MHz, DMSO, δ in ppm): 12.12 (ls, 1H); 8.38 (d, 1H, J=8.1 Hz); 7.80 (d, 1H, J=7.4 Hz); 7.70 (s, 1H); 7.61 (t, 1H, J=7.8 Hz); 7.45 (s, 1H); 7.29 (s, 1H); 3.64 (d, 1H, J=12.3 Hz); 2.88 (d, 1H, J=12.3 Hz); 2.09 (s, 3H).

Example 32

5-(5-chloro-1-benzothien-2-yl)-8-methyl-1,9-dihydro-2H-[1,3]-oxazolo[4,5-h][2,3]benzodiazepin-2-one The title product is obtained according to the procedure described in Example 6 using 5-chloro-1-benzothiophene-2-carbaldehyde instead of 1-benzothiophene-2-carbaldehyde.
Melting point: 322-324° C.
$^1$H NMR spectroscopic analysis (500 MHz, DMSO, δ in ppm); 12.11 (ls, 1H); 8.03 (d, 1H, J=8.7 Hz); 7.95 (d, 1H, J=2.1 Hz); 7.68 (s, 1H); 7.52 (s, 1H); 7.44 (dd, 1H, J1=2.1 Hz, J2=8.5 Hz); 7.38 (s, 1H); 3.62 (d, 1H, J=12.5 Hz); 2.86 (d, 1H, J=12.2 Hz); 2.08 (s, 3H).

Example 33

5-(5-chloro-3-methyl-1-benzothien-2-yl)-8-methyl-1,9-dihydro-2H-[1,3]oxazolo[4,5-h][2,3]benzodiazepin-2-one The title product is obtained according to the procedure described in Example 6 using 5-chloro-3-methyl-1-benzothiophene-2-carbaldehyde instead of 1-benzothiophene-2-carbaldehyde.
Melting point: 310-312° C.

Example 34

5-(5-fluoro-3-methyl-1-benzothien-2-yl)-8-methyl-1,9-dihydro-2H-[1,3]oxazolo[4,5-h][2,3]benzodiazepin-2-one The title product is obtained according to the procedure described in Example 6 using 5-fluoro-3-methyl-1-benzothiophene-2-carbaldehyde instead of 1-benzothiophene-2-carbaldehyde.
Melting point: 291-292° C.

Example 35

8-methyl-5-[5-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 5-(trifluoromethyl)-1-benzothiophene-2-carbaldehyde instead of 2-naphthaldehyde.
Melting point: 282-284° C.

Example 36

5-(6-fluoro-1-benzothien-2-yl)-8-methyl-1,9-dihydro-2H-[1,3]oxazolo[4,5-h][2,3]benzodiazepin-2-one The title product is obtained according to the procedure described in Example 6 using 6-fluoro-1-benzothiophene-2-carbaldehyde instead of 1-benzothiophene-2-carbaldehyde.
Melting point: 345-347° C.

Example 37

5-(6-fluoro-3-methyl-1-benzothien-2-yl)-8-methyl-1,9-dihydro-2H-[1,3]oxazolo[4,5-h][2,3]benzodiazepin-2-one The title product is obtained according to the procedure described in Example 1 using 6-fluoro-3-methyl-1-benzothiophene-2-carbaldehyde instead of 2-naphthaldehyde.
Melting point: 286-288° C.

Example 38

8-methyl-5-[6-(trifluoromethyl)-1-benzothien-2-yl]-1,9-dihydro-2H-[1,3]oxazolo[4,5-h][2,3]benzodiazepin-2-one The title product is obtained according to the procedure described in Example 6 using 6-(trifluoromethyl)-1-benzothiophene-2-carbaldehyde instead of 1-benzothiophene-2-carbaldehyde.
Melting point: 329-331° C.

Example 39

2-(8-methyl-2-oxo-1,9-dihydro-2H-[1,3]oxazolo[4,5-h][2,3]benzodiazepin-5-yl)-1-benzothiophene-6-carbonitrile The title product is obtained according to the procedure described in Example 6 using 2-formyl-1-benzofuran-6-carbonitrile instead of 1-benzothiophene-2-carbaldehyde.
Melting point: 388-390° C.

Example 40

5-(7-fluoro-1-benzothien-2-yl)-8-methyl-1,9-dihydro-2H-[1,3]-oxazolo[4,5-h][2,3]benzodiazepin-2-one The title product is obtained according to the procedure described in Example 1 using 7-fluoro-1-benzothiophene-2-carbaldehyde instead of 2-naphthaldehyde.
Melting point: 324-326° C.
$^1$H NMR spectroscopic analysis (500 MHz, DMSO, δ in ppm): 12.09 (bs, 1H); 7.73 (m, 1H); 7.70 (s, 1H); 7.63 (d, 1H, J=3.7 Hz); 7.42 (m, 1H); 7.29 (m, 1H); 7.27 (s, 1H); 3.62 (d, 1H, J=12.5 Hz); 2.86 (d, 1H, J=12.3 Hz); 2.08 (s, 3H).

Example 41

5-(7-fluoro-3-methyl-1-benzothien-2-yl)-8-methyl-1,9-dihydro-2H-[1,3]oxazolo[4,5-h][2,3]benzodiazepin-2-one The title product is obtained according to the procedure described in Example 1 using 7-fluoro-3-methyl-1-benzothiophene-2-carbaldehyde instead of 2-naphthaldehyde.
Melting point: 307-309° C.

Example 42

5-(7-chloro-1-benzothien-2-yl)-8-methyl-1,9-dihydro-2H-[1,3]-oxazolo[4,5-h][2,3]benzodiazepin-2-one The title product is obtained according to the procedure described in Example 1 using 7-chloro-1-benzothiophene-2-carbaldehyde instead of 2-naphthaldehyde.
Melting point: 333-335° C.

Example 43

5-(7-chloro-4-fluoro-1-benzothien-2-yl)-8-methyl-1,9-dihydro-2H-[1,3]oxazolo[4,5-h][2,3]benzodiazepin-2-one The title product is obtained according to the procedure described in Example 1 using 7-chloro-4-fluoro-1-benzothiophene-2-carbaldehyde instead of 2-naphthaldehyde.
Melting point: 364-366° C.

Example 44

5-(7-chloro-4-fluoro-3-methyl-1-benzothien-2-yl)-8-methyl-1,9-dihydro-2H-[1,3]oxazolo[4,5-h][2,3]benzodiazepin-2-one The title product is obtained according to the procedure described in Example 8 using 7-chloro-4-fluoro-3-methyl-1- benzothiophene-2-carbaldehyde instead of 3-chloro-6-fluoro-1-benzothiophene-2-carbaldehyde.
Melting point: 319-320° C.

Example 45

5-[7-chloro-4-(trifluoromethyl)-1-benzothien-2-yl]-8-methyl-1,9-dihydro-2H-[1,3]oxazolo[4,5-h][2,3]benzodiazepin-2-one The title product is obtained according to the procedure described in Example 1 using 7-chloro-4-(trifluoromethyl)-1-benzothiophene-2-carbaldehyde instead of 2-naphthaldehyde.
Melting point: 340-342° C.

Example 46

5-(7-bromo-4-fluoro-1-benzothien-2-yl)-8-methyl-1,9-dihydro-2H-[1,3]oxazolo[4,5-h][2,3]benzodiazepin-2-one The title product is obtained according to the procedure described in Example 1 using 7-bromo-4-fluoro-1-benzothiophene-2-carbaldehyde instead of 2-naphthaldehyde.
Melting point: 345-347° C.

Example 47

8-methyl-5-[7-(trifluoromethyl)-1-benzothien-2-yl]-1,9-dihydro-2H-[1,3]oxazolo[4,5-h][2,3]benzodiazepin-2-one The title product is obtained according to the procedure described in Example 1 using 7-(trifluoromethyl)-1-benzothiophene-2-carbaldehyde instead of 2-naphthaldehyde.
Melting point: 336-338° C.

Example 48

8-methyl-5-(1-methylnaphtho[2,1-b]thien-2-yl)-1,9-dihydro-2H-[1,3]oxazolo[4,5-h][2,3]benzodiazepin-2-one The title product is obtained according to the procedure described in Example 8 using 1-methylnaphtho[2,1-b]thiophene-2-carbaldehyde instead of 3-chloro-6-fluoro-1-benzothiophene-2-carbaldehyde.
Melting point: 318-320° C.

Example 49

8-ethyl-5-(4-fluoro-1-benzothien-2-yl)-1,5-dihydro-2H-[1,3]oxazolo[4,5-h][2,3]benzodiazepin-2-one The title product is obtained according to the procedure described in Example 1 using 4-fluoro-1-benzothiophene-2-carbaldehyde instead of 2-naphthaldehyde and the compound of Preparation 4 instead of the compound of Preparation 1.
Melting point: 295-297° C.

Example 50

8-ethyl-5-[4-(trifluoromethyl)-1-benzothien-2-yl]-1,5-dihydro-2H-[1,3]oxazolo[4,5-h][2,3]benzodiazepin-2-one The title product is obtained according to the procedure described in Example 1 using 4-(trifluoromethyl)-1-benzothiophene-2-carbaldehyde instead of 2-naphthaldehyde and the compound of Preparation 4 instead of the compound of Preparation 1.
Melting point: 301-303° C.

Example 51

8-ethyl-5-[4-fluoro-3-methyl-1-benzothien-2-yl]-1,5-dihydro-2H-[1,3]oxazolo[4,5-h][2,3]benzodiazepin-2-one The title product is obtained according to the procedure described in Example 1 using 4-fluoro-3-methyl-1-benzothiophene-2-carbaldehyde instead of 2-naphthaldehyde and the compound of Preparation 4 instead of the compound of Preparation 1.
Melting point: 289-291° C.

Example 52

5-(5-fluoro-1-benzothien-2-yl)-8-methyl-1,9-dihydro-2H-[1,3]oxazolo[4,5-h][2,3]benzodiazepin-2-one The title product is obtained according to the procedure described in Example 1 using 5-fluoro-1-benzothiophene-2-carbaldehyde instead of 2-naphthaldehyde.
Melting point: 291-293° C.

Pharmacological Study

Example A $GABA_A$ Receptor Activity Study

The compounds are tested on HEK-293 (Human Embryonic Kidney) cells stably expressing the subunit $\alpha_5$ of the human $GABA_A$ receptor, and also the subunits beta2 (short) and gamma2 (long). The cells are maintained in the presence of a selection of three antibiotics—neomycin, zeocin and puromycin—in a Dulbecco medium (DMEM) containing 10% (v/v) foetal bovine serum. On the day before the experiment, the cells are transferred to 96-well plates (in a density of 50,000 cells/well). The cells are then preincubated for 40 minutes with the compounds under test and are treated with GABA. The membrane potential is monitored using a blue FMP marker (Molecular Devices), following the instructions of the manufacturer. The responses are recorded for 120 seconds on a FlexStation3 plate reader (Molecular Devices, USA). The $IC_{50}$ values of the tested compounds are determined by curve adjustment obtained by non-linear regression using SoftMax Pro software (Molecular Devices, USA).

|  | alpha5 $IC_{50}$ [nM] |
|---|---|
| Example 5 | 430 |
| Example 6 | 130 |
| Example 9 | 250 |
| Example 21 | 200 |
| Example 31 | 500 |
| Example 32 | 172 |
| Example 36 | 100 |
| Example 40 | 227 |

The compounds of the invention consequently exhibit excellent affinity and are selective for the alpha5 receptor.

Example B

Test for Recognition of New Objects, in the Mouse

This test measures non-spatial working memory in the rodent. It is based on the natural tendency of the animal to spend more time exploring a new object than a familiar object. The wish to explore a new object demonstrates use of learning and recognition memory.

On Day 0 (familiarisation phase), male NMRI mice are placed in a black PVC box (32×45×27 cm) without an object, for 2.5 minutes. On the first day the mice are free to explore two identical objects for 3 minutes (acquisition phase). On the second day one of the objects is replaced by a new object and the duration of exploration is timed for each object over a period of 4 minutes (retention phase). Pretreatment with the compounds of the invention is carried out by the i.p. route on the day of the acquisition phase. The duration of exploration is measured by the TSE System software (TSE System GmbH, Bad Homburg, Germany), Results:

FIGS. 1, 2 and 3, demonstrate the procognitive effect of the compound of Examples 21, 31 and 36, respectively, in the object recognition model in the mouse after i.p. administration (approx. at the concentration peak). The results show that the compounds of the invention demonstrate a procognitive effect in the object recognition model in the mouse. In particular, the compound of Example 21 has a significant procognitive effect at doses of 0.01, 0.03 and 0.1 mg/kg, i.p. Moreover, the compound of Example 31 has a significant procognitive effect at dose of 1 mg/kg, i.p. and the compound of Example 36 has a significant precognitive effect at dose of 10 mg/kg, i.p.

Example C

Radial Maze Test in the Rat

This test is widely used to evaluate working and referential memory in the rodent. The apparatus consists of a small central octagonal platform from which there radiate eight different, equally spaced corridors. At the end of each corridor there is food, which is not visible from the central platform. In the experiment, all the corridors contain a reward and the animal has to visit each of the corridors just once. Each further visit is considered an error.

On the first day of the experiment the rats are deprived of food for 24 hours. Learning starts on the following day. The rats are placed on the central platform of the maze, each of the eight corridors having been provided with food. The animals are free to eat the food in the eight corridors. If a rat has not eaten all of the food within 20 minutes, it is withdrawn from the maze.

The experiments are continued once a day until the animals attain the determined objective, namely obtaining a total number of errors—that is to say, of any further visits to a corridor—of less than 3. These animals are included in the rest of the study. On the last day, the selected rats are treated p.o. with ketamine (10 mg/kg i.p.) co-administered either with a carrier or with a compound of the invention. The tests start 120 minutes after administration. Each test lasts a maximum of 5 minutes.

Results:

The results show in FIG. 4 that the compounds of the invention demonstrate significant improvement of the memory of the animals tested. In particular, the compound of Example 21 significantly reverses the ketamine-induced referential memory deficit in dose-dependent manner (from 0.3 to 3 mg/kg p.o.).

Example D

Occlusion of the Middle Cerebral Artery (MCA) in the Mouse

Permanent focal cerebral ischaemia is produced by electrocoagulation of the left MCA (according to the method of Welsh F A et al., *J. Neurochem.* 1987, 49, 846-851). Male NMRI mice are anaesthetised using 2,2,2-tribromoethanol (500 mg/kg i.p., 20 ml/kg). An incision is made in the left temporo-parietal region of the head between the orbit and the ear. The temporal muscle is then incised and folded back to expose the skull. A small trepanation hole is drilled in the outer lateral part of the skull just to the level of the MCA, and the trunk of the MCA is then occluded by electrocoagulation.

The compounds of the invention are administered by the i.p. route 30 minutes after occlusion of the MCA. Two days later, the animals are deeply anaesthetised using sodium pentobarbital (60 mg/kg i.p., 10 ml/kg) perfused through the heart with a 4% 2,3,5-triphenyltetrazolium chloride solution. The animals are finally decapitated, and the brains are extracted and placed for at least 24 hours in a saline solution containing 8% formaldehyde. Measurement of the necrosed surface area is determined using an image analysis system (DigiCell for Windows 4.0).

Results:

The results show in FIG. 5 that the compounds of the invention demonstrate a significant neuroprotective effect. In particular, the compound of Example 21 significantly inhibits cerebral damage at doses of 1, 3 and 10 mg/kg i.p. in the MCA occlusion model in the mouse.

Example E

Pharmaceutical Composition

| Formula for the preparation of 1000 tablets each containing 10 mg of 5-(4-fluoro-1-benzothien-2-yl)-8-methyl-1,9-dihydro-2H-[1,3]oxazolo[4,5-h][2,3]benzodiazepin-2-one | |
|---|---|
| (Example 21) | 10 g |
| Hydroxypropylcellulose | 2 g |
| Wheat starch | 10 g |
| Lactose | 100 g |
| Magnesium stearate | 3 g |
| Talc | 3 g |

The invention claimed is:

1. A compound selected from those of formula (I):

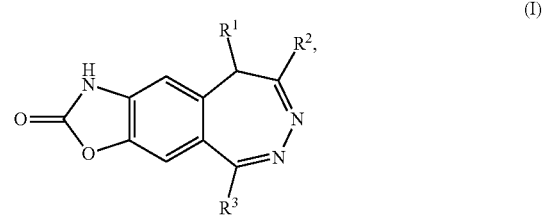

(I)

wherein:
R¹ represents a hydrogen atom or a linear or branched $(C_1-C_4)$alkyl group;
R² represents a linear or branched $(C_1-C_4)$alkyl group;
R³ represents an aryl or heteroaryl group;
and positional isomers, enantiomers, diastereoisomers, and addition salts thereof with a pharmaceutically acceptable acid, and complexes and adducts thereof.

2. The compound of claim 1, wherein R¹ represents a hydrogen atom.

3. The compound of claim 1, wherein R² represents a methyl group.

4. The compound of claim 1, wherein R³ represents a heteroaryl group.

5. The compound of claim 1, wherein R³ represents a bicyclic aromatic group having from 1 to 3 identical or different hetero atoms selected from nitrogen, oxygen and sulphur, optionally substituted by one or more identical or different groups selected from a halogen atom; a linear or branched $(C_1-C_6)$alkyl group which is unsubstituted or substituted by one or more halogen atoms; a linear or branched $(C_1-C_6)$alkoxy group; a linear or branched $(C_1-C_6)$alkylcarbonyl group; a carboxy group; a linear or branched $(C_1-C_6)$ alkoxycarbonyl group; a hydroxy group; a cyano group; a nitro group; an aminocarbonyl group which is unsubstituted or substituted by one or more linear or branched $(C_1-C_6)$alkyl groups; and an amino group which is unsubstituted or substituted by one or two linear or branched $(C_1-C_6)$alkyl groups.

6. The compound of claim 1, wherein R³ represents a benzothienyl or quinolyl group, optionally substituted by one or more identical or different groups selected from a halogen atom and a linear or branched $(C_1-C_4)$alkyl group which is unsubstituted or substituted by one or more halogen atoms.

7. The compound of claim 1, wherein R³ represents a 1-benzothienyl group, optionally substituted by one or more identical or different groups selected from a halogen atom and a linear or branched $(C_1-C_4)$alkyl group which is unsubstituted or substituted by one or more halogen atoms.

8. The compound of claim 1, wherein R³ represents a 1-benzothien-2-yl group, optionally substituted by one or more identical or different groups selected from a halogen atom and a linear or branched $(C_1-C_4)$alkyl group which is unsubstituted or substituted by one or more halogen atoms.

9. The compound of claim 1, wherein R³ represents a 1-benzothien-2-yl group, optionally substituted by one or more identical or different groups selected from a fluorine atom, a chlorine atom, a trifluoromethyl group and a methyl group.

10. The compound of claim 1, which is selected from:
5-(4-fluoro-1-benzothien-2-yl)-8-methyl-1,9-dihydro-2H-[1,3]oxazolo[4,5-h][2,3]-benzodiazepin-2-one;
8-methyl-5-(6-quinolyl-1,9-dihydro-2H-[1,3]oxazolo[4,5-h][2,3]benzodiazepin-2-one;
5-(1-benzothien-2-yl)-8-methyl-1,9-dihydro-2H-[1,3]oxazolo[4,5-h][2,3]benzodiazepin-2-one;
5-(5-chloro-1-benzothien-2-yl)-8-methyl-1,9-dihydro-2H-[1,3]oxazolo[4,5-h][2,3]-benzodiazepin-2-one;
5-[3-chloro-4-(trifluoromethyl)-1-benzothien-2-yl]-8-methyl-1,9-dihydro-2H-[1,3]oxazolo[4,5-h][2,3]benzodiazepin-2-one;
8-methyl-5-[4-(trifluoromethyl)-1-benzothien-2-yl]-1,9-dihydro-2H-[1,3]oxazolo[4,5-h][2,3]benzodiazepin-2-one;
5-(6-fluoro-1-benzothien-2-yl)-8-methyl-1,9-dihydro-2H-[1,3]oxazolo[4,5-h][2,3]-benzodiazepin-2-one;
5-(7-fluoro-1-benzothien-2-yl)-8-methyl-1,9-dihydro-2H-[1,3]oxazolo[4,5-h][2,3]-benzodiazepin-2-one.

11. A pharmaceutical composition comprising as active ingredient a compound of claim 1 in combination with one or more inert, non-toxic, pharmaceutically acceptable carriers.

12. A method for treating a condition selected from schizophrenia, unipolar depression, Alzheimer's disease, vascular dementia, autism spectrum disorders, Down's syndrome, fragile X syndrome, Parkinson's disease, Huntington's disease, generalised anxiety, panic disorder with or without agoraphobia, obsessive-compulsive disorders, post-traumatic stress disorders, bipolar disorders, sequalae of a cerebral vascular accident and sequalae of brain, spine or medullary trauma in a subject in need thereof, comprising administration of an effective amount of a compound of claim 1.

\* \* \* \* \*

UNITED STATES PATENT AND TRADEMARK OFFICE
CERTIFICATE OF CORRECTION

PATENT NO. : 8,778,932 B2  
APPLICATION NO. : 13/413977  
DATED : July 15, 2014  
INVENTOR(S) : István Ling et al.

Page 1 of 1

It is certified that error appears in the above-identified patent and that said Letters Patent is hereby corrected as shown below:

Title Page, item (75), Inventor address: "Gascályi" should be --Gacsályi--

Title Page, item (56), Other Publications: "Klumpers, et al., Eur. J. Nucl. Med. Mol. Imaging, 2010, 27" should be
--Klumpers, et al., Eur. J. Nucl. Med. Mol. Imaging, 2010, 37--

Signed and Sealed this  
Twenty-fifth Day of November, 2014

Michelle K. Lee  
*Deputy Director of the United States Patent and Trademark Office*